US011363820B2

(12) United States Patent
Ono

(10) Patent No.: US 11,363,820 B2
(45) Date of Patent: Jun. 21, 2022

(54) METHOD FOR SELECTING PLANT SYMBIOTIC MICROBES, AND MICROBIAL MIXTURE

(71) Applicant: SEKISUI CHEMICAL CO., LTD., Osaka (JP)

(72) Inventor: Seigo Ono, Tsukuba (JP)

(73) Assignee: SEKISUI CHEMICAL CO., LTD., Osaka (JP)

(*) Notice: Subject to any disclaimer, the term of this patent is extended or adjusted under 35 U.S.C. 154(b) by 209 days.

(21) Appl. No.: 16/348,740

(22) PCT Filed: Dec. 8, 2017

(86) PCT No.: PCT/JP2017/044161
§ 371 (c)(1),
(2) Date: May 9, 2019

(87) PCT Pub. No.: WO2018/105722
PCT Pub. Date: Jun. 14, 2018

(65) Prior Publication Data
US 2019/0297894 A1 Oct. 3, 2019

Related U.S. Application Data

(60) Provisional application No. 62/488,069, filed on Apr. 21, 2017, provisional application No. 62/449,122, filed on Jan. 23, 2017, provisional application No. 62/449,118, filed on Jan. 23, 2017, provisional application No. 62/434,427, filed on Dec. 15, 2016, provisional application No. 62/431,443, filed on Dec. 8, 2016.

(51) Int. Cl.
A01N 63/00 (2020.01)
A01N 63/22 (2020.01)
A01G 7/06 (2006.01)
C12N 1/20 (2006.01)
A01G 7/00 (2006.01)
C12N 1/00 (2006.01)

(52) U.S. Cl.
CPC .............. A01N 63/22 (2020.01); A01G 7/00 (2013.01); A01G 7/06 (2013.01); C12N 1/00 (2013.01); C12N 1/20 (2013.01)

(58) Field of Classification Search
CPC .................................. A01G 7/06; C12N 1/00
See application file for complete search history.

(56) References Cited

FOREIGN PATENT DOCUMENTS

| JP | 2009-195124 | 9/2009 |
|---|---|---|
| JP | 2015-528296 | 9/2015 |
| JP | 2015-530093 | 10/2015 |
| WO | 2012/125050 | 9/2012 |
| WO | WO-2012125050 A9 * | 2/2013 ............ A01H 17/00 |
| WO | 2014/036474 | 3/2014 |
| WO | 2014/046553 | 3/2014 |

OTHER PUBLICATIONS

Suzaki T, et al. Chapter Three—Leguminous Plants: Inventors of Root Nodules to Accommodate Symbiotic Bacteria. International Review of Cell and Molecular Biology. Academic Press 2015. vol. 316, pp. 111-158 (Year: 2015).*
Viscardi, S. Sep. 2016. Assessment of plant growth promoting activities and abiotic stress tolerance of Azotobacter chroococcum strains for a potential use in sustainable agriculture. Journal of soil science and plant nutrition, 16(3), pp. 848-863. (Year: 2016).*
International Search Report dated Jan. 16, 2018 in International (PCT) Application No. PCT/JP2017/044161.
Kang et al., "Plant growth-promoting rhizobacteria reduce adverse effects of salinity and osmotic stress by regulating phytohormones and antioxidants in *Cucumis sativus*", Journal of Plant Interactions, 2014, vol. 9, No. 1, pp. 673-682.
Tiwari et al., "Salt-tolerant rhizobacteria-mediated induced tolerance in wheat (*Triticum aestivum*) and chemical diversity in rhizosphere enhance plant growth", Biol. Fertil Soils, 2011, vol. 47, pp. 907-916.
Damodaran et al., "Rhizosphere and endophytic bacteria for induction of salt tolerance in gladiolus grown in sodic soils", J. Plant Interact., 2014, vol. 9, No. 1, pp. 577-584.
Wang et al., "Survey of plant drought-resistance promoting bacteria from populus euphratica tree living in arid area", Indian J. Microbial., 2014, vol. 54, No. 4, pp. 419-426.
Marasco et al., "A drought resistance-promoting microbiome is selected by root system under desert farming", PLOS One, 2012, vol. 7, No. 10, e48479, pp. 1-14.
Wang et al., "Induction of drought tolerance in cucumber plants by a consortium of three plant growth-promoting rhizobacterium strains", PLOS One, 2012, vol. 7, No. 12, e52565 pp. 1-10.

(Continued)

*Primary Examiner* — Bin Shen
(74) *Attorney, Agent, or Firm* — Wenderoth, Lind & Ponack, L.L.P.

(57) ABSTRACT

The present invention provides a screening method for selecting plant symbiotic microorganisms enabling plant growth under abiotic stress and/or biotic stress, a microbial mixture of microorganisms which are selected from nature by the method and enables a plant to grow under salinity stress and/or hyperosmotic stress in symbiosis with the plant. Specifically, the present invention provides a screening method for selecting plant symbiotic microorganisms, comprising a first screening step of allowing at least one plant to grow for a predetermined period of time while being partially soaked in a solution containing a microbial mixture under abiotic stress and/or biotic stress, and collecting microorganisms adhering to grown plant to thereby select out the microorganisms as plant symbiotic microorganisms enabling plant growth under the stress.

15 Claims, 1 Drawing Sheet
Specification includes a Sequence Listing.

(56) References Cited

OTHER PUBLICATIONS

"Bacillus pumilus strain CSR-B-2 16S ribosomal RNA gene", partial sequence, GenBank accession No. JQ768236, Mar. 13, 2013, [retrieved on Dec. 25, 2017], retrieved from the Internet, URL, https://www.ncbi.nlm.nih.gov/nuccore/JQ768236.
Kamilova et al., "Enrichment for enhanced competitive plant root tip colonizers selects for a new class of biocontrol bacteria", Environ. Microbiol., 2005, vol. 7, No. 11, pp. 1809-1817.
Naveed et al., "Increased drought stress resilience of maize through endophytic colonization by *Burkholderia phytofirmans* PsJN and *enterobacter* sp.FD17", Environ. Exp. Bot., 2014, vol. 97, pp. 30-39.
Kumar et al., "Synergistic effect of pseudomonas putida and *Bacillus amyloliquefaciens* ameliorates drought stress in chickpea (*Cicer arietinum* L.)", Plant Signal. Behav., Jan. 2016, vol. 11, No. 1, e1071004, pp. 1-9.
Kuiper et al., "Selection of a plant-bacterium pair as a novel tool for rhizostimulation of polycyclic aromatic hydrocarbon-degrading bacteria", Mol. Plant Microbe Interact., 2001, vol. 14, No. 10, pp. 1197-1205
Zhang et al., "Isolation and identification of drought-tolerant bacteria from xerophtes", Shipin Kexue, 2012, vol. 33, No. 5, pp. 124-128.
Verslues et al., "Methods and concepts in quantifying resistance to drought, salt and freezing, abiotic stresses that affect plant water status", Plant J., 2006, vol. 45, pp. 523-539.
Swenson et al., "Artificial ecosystem selection", Proc. Natl. Acad. Sci. USA, 2000, vol. 97, No. 16, pp. 9110-9114.

\* cited by examiner

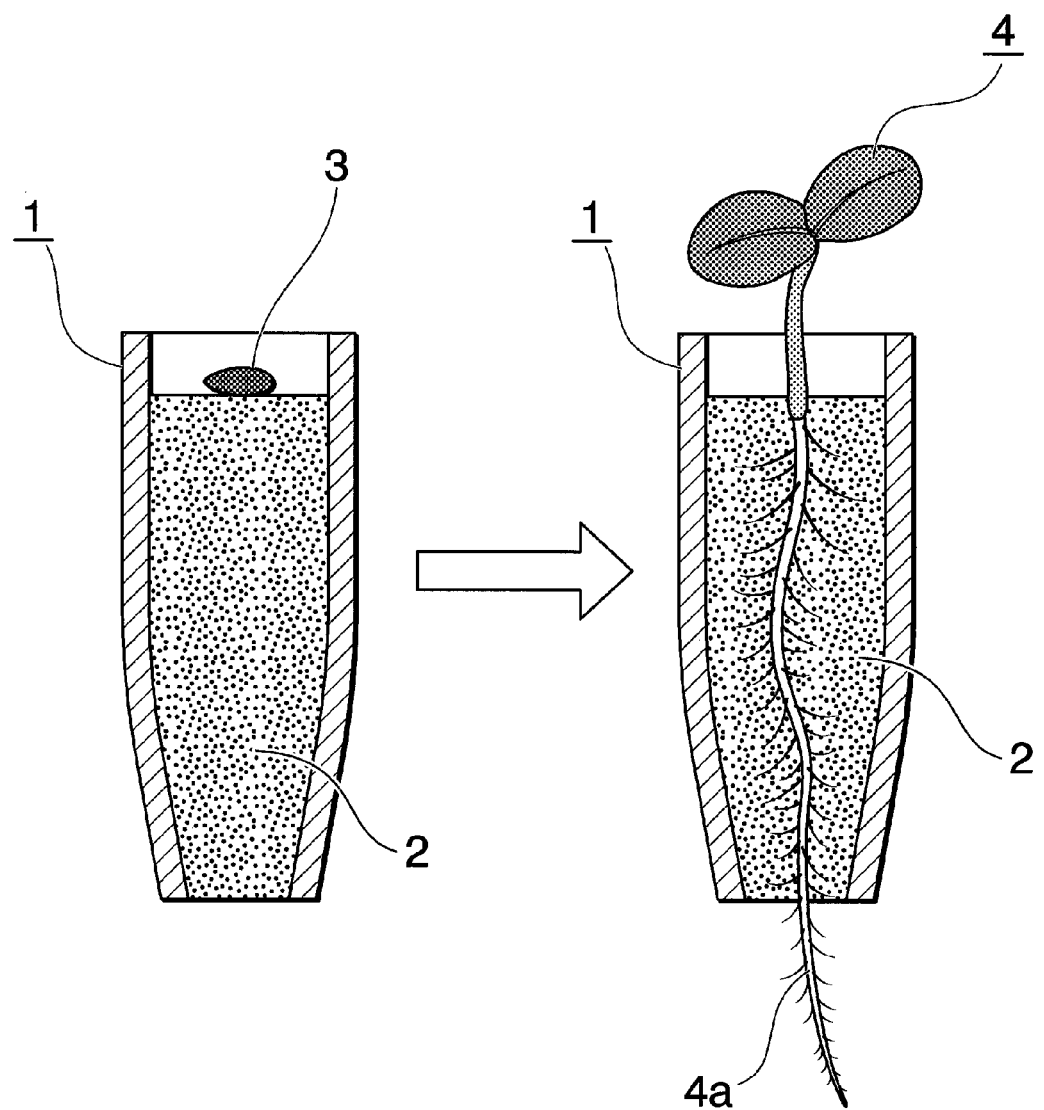

```
                        SEQUENCE LISTING

<160> NUMBER OF SEQ ID NOS: 7

<210> SEQ ID NO 1
<211> LENGTH: 1513
<212> TYPE: DNA
<213> ORGANISM: Bacillus pumilus CRCO-1

<400> SEQUENCE: 1
agagtttgat catggctcag gacgaacgct ggcggcgtgc ctaatacatg caagtcgagc      60
ggacagaagg gagcttgctc ccggatgtta gcggcggacg ggtgagtaac acgtgggtaa     120
cctgcctgta agactgggat aactccggga aaccggagct aataccggat agttccttga    180
accgcatggt tcaaggatga aagacggttt cggctgtcac ttacagatgg acccgcggcg    240
cattagctag ttggtggggt aatggctcac caaggcgacg atgcgtagcc gacctgagag    300
ggtgatcggc cacactggga ctgagacacg gcccagactc ctacgggagg cagcagtagg    360
gaatcttccg caatggacga aagtctgacg gagcaacgcc gcgtgagtga tgaaggtttt    420
cggatcgtaa agctctgttg ttagggaaga acaagtgcga gagtaactgc tcgcaccttg    480
acggtaccta accagaaagc cacggctaac tacgtgccag cagccgcggt aatacgtagg    540
tggcaagcgt tgtccggaat tattgggcgt aaagggctcg caggcggttt cttaagtctg    600
atgtgaaagc ccccggctca accggggagg gtcattggaa actgggaaac ttgagtgcag    660
aagaggagag tggaattcca cgtgtagcgg tgaaatgcgt agagatgtgg aggaacacca    720
gtggcgaagg cgactctctg gtctgtaact gacgctgagg agcgaaagcg tggggagcga    780
acaggattag ataccctggt agtccacgcc gtaaacgatg agtgctaagt gttaggggggt    840 ttccgcccct tagtgctgca gctaacgcat taagcactcc gcctggggag tacggtcgca    900
agactgaaac tcaaaggaat tgacggggc ccgcacaagc ggtggagcat gtggtttaat     960
tcgaagcaac gcgaagaacc ttaccaggtc ttgacatcct ctgacaaccc tagagatagg    1020
gctttccctt cggggacaga gtgacaggtg gtgcatggtt gtcgtcagct cgtgtcgtga    1080
gatgttgggt taagtcccgc aacgagcgca acccttgatc ttagttgcca gcatttagtt    1140
gggcactcta aggtgactgc cggtgacaaa ccggaggaag gtggggatga cgtcaaatca    1200
tcatgcccct tatgacctgg gctacacacg tgctacaatg gacagaacaa agggctgcga    1260
gaccgcaagg tttagccaat cccataaatc tgtcctcagt tcggatcgca gtctgcaact    1320
```

| | |
|---|---|
| cgactgcgtg aagctggaat cgctagtaat cgcggatcag catgccgcgg tgaatacgtt | 1380 |
| cccgggcctt gtacacaccg cccgtcacac cacgagagtt tgcaacaccc gaagtcggtg | 1440 |
| aggtaacctt tatggagcca gccgccgaag gtggggcaga tgattggggt gaagtcgtaa | 1500 |
| caaggtaacc gta | 1513 |

<210> SEQ ID NO 2
<211> LENGTH: 1513
<212> TYPE: DNA
<213> ORGANISM: Bacillus pumilus CRCO-2

<400> SEQUENCE: 2

| | |
|---|---|
| agagtttgat catggctcag gacgaacgct ggcggcgtgc ctaatacatg caagtcgagc | 60 |
| gaacagaagg gagcttgctc ccggatgtta gcggcggacg ggtgagtaac acgtgggtaa | 120 |
| cctgcctgta agactgggat aactccggga aaccggagct aataccggat agttccttga | 180 |
| accgcatggt tcaaggatga agacggtttt cggctgtcac ttacagatgg acccgcggcg | 240 |
| cattagctag ttggtggggt aatggctcac caaggcgacg atgcgtagcc gacctgagag | 300 |
| ggtgatcggc cacactggga ctgagacacg gcccagactc ctacgggagg cagcagtagg | 360 |
| gaatcttccg caatggacga aagtctgacg gagcaacgcc gcgtgagtga tgaaggtttt | 420 |
| cggatcgtaa agctctgttg ttagggaaga acaagtgcga gagtaactgc tcgcaccttg | 480 |
| acggtaccta accagaaagc cacggctaac tacgtgccag cagccgcggt aatacgtagg | 540 |
| tggcaagcgt tgtccggaat tattgggcgt aaagggctcg caggcggttt cttaagtctg | 600 |
| atgtgaaagc cccggctcaa ccggggaggg tcattggaaa ctgggaaac ttgagtgcag | 660 |
| aagaggagag tggaattcca cgtgtagcgg tgaaatgcgt agagatgtgg aggaacacca | 720 |
| gtggcgaagg cgactctctg gtctgtaact gacgctgagg agcgaaagcg tggggagcga | 780 |
| acaggattag ataccctggt agtccacgcc gtaaacgatg agtgctaagt gttacggggt | 840 |
| ttccgccccct tagtgctgca gctaacgcat taagcactcc gcctggggag tacggtcgca | 900 |
| agactgaaac tcaaaggaat tgacgggggc ccgcacaagc ggtggagcat gtggtttaat | 960 |
| tcgaagcaac gcgaagaacc ttaccaggtc ttgacatcct ctgacaaccc tagagatagg | 1020 |
| gctttccctt cggggacaga gtgacaggtg gtgcatggtt gtcgtcagct cgtgtcgtga | 1080 |
| gatgttgggt taagtcccgc aacgagcgca acccttgatc ttagttgcca gcatttagtt | 1140 |
| gggcactcta aggtgactgc cggtgacaaa ccggaggaag gtgggatga cgtcaaatca | 1200 |
| tcatgcccct tatgacctgg gctacacacg tgctacaatg gacagaacaa agggctgcga | 1260 |
| gaccgcaagg tttagccaat cccataaatc tgttctcagt tcggatcgca gtctgcaact | 1320 |
| cgactgcgtg aagctggaat cgctagtaat cgcggatcag catgccgcgg tgaatacgtt | 1380 |
| cccgggcctt gtacacaccg cccgtcacac cacgagagtt tgcaacaccc gaagtcggtg | 1440 |
| aggtaacctt tatggagcca gccgccgaag gtggggcaga tgattggggt gaagtcgtaa | 1500 |
| caaggtaacc gta | 1513 |

<210> SEQ ID NO 3
<211> LENGTH: 1513
<212> TYPE: DNA
<213> ORGANISM: Bacillus pumilus CRCO-3

<400> SEQUENCE: 3

| | |
|---|---|
| agagtttgat catggctcag gacgaacgct ggcggcgtgc ctaacacatg caagtcgagc | 60 |
| gaacagaagg gagcttgctc ccggatgtta gcggcggacg ggtgagtaac acgtgggtaa | 120 |

```
cctgcctgta agactgggat aactccggga aaccggagct aataccggat agttccttga    180
accgcatggt tcaaggatga agacggtttt cggctgtcac ttacagatgg acccgcggcg    240
cattagctag ttggtggggt aatggctcac caaggcgacg atgcgtagcc gacctgagag    300
ggtgatcggc cacactggga ctgagacacg gcccagactc ctacgggagg cagcagtagg    360
gaatcttccg caatggacga aagtctgacg gagcaacgcc gcgtgagtga tgaaggtttt    420
cggatcgtaa agctctgttg ttagggaaga caagtgcga gagtaactgc tcgcaccttg    480
acggtaccta accagaaagc cacggctaac tacgtgccag cagccgcggt aatacgtagg    540
tggcaagcgt tgtccggaat tattgggcgt aaagggctcg caggcggttt cttaagtctg    600
atgtgaaagc ccccggctca accggggagg gtcattggaa actgggaaac ttgagtgcag    660
aagaggagag tggaattcca cgtgtagcgg tgaaatgcgt agagatgtgg aggaacacca    720
gtggcgaagg cgactctctg gtctgtaact gacgctgagg agcgaaagcg tggggagcga    780
acaggattag ataccctggt agtccacgcc gtaaacgatg agtgctaagt gttaggggt    840
ttccgcccct tagtgctgca gctaacgcat taagcactcc gcctggggaa tacggtcgca    900
agactgaaac tcaaaggaat tgacggggc cgcacaagc ggtggagcat gtggtttaat    960
tcgaagcaac gcgaagaacc ttaccaggtc ttgacatcct ctgacaaccc tagagatagg   1020
gctttccctt cggggacaga gtgacaggtg gtgcatggtt gtcgtcagct cgtgtcgtga   1080
gatgttgggt taagtcccgc aacgagcgca acccttgatc ttagttgcca gcatttagtt   1140
gggcactcta aggtgactgc cggtgacaaa ccggaggaag gtggggatga cgtcaaatca   1200
tcatgcccct tatgacctgg gctacacacg tgctacaatg gacagaacaa agggctgcga   1260
gaccgcaagg tttagccaat cccataaatc tgttctcagt tcggatcgca gtctgcaact   1320
cgactgcgtg aagctggaat cgctagtaat cgcggatcag catgccgcgg tgaatacgtt   1380
cccgggcctt gtacacaccg cccgtcacac cacgagagtt tgcaacaccc gaagtcggtg   1440
aggtaacctt tatggagcca gccgccgaag gtggggcaga tgattggggt gaagtcgtaa   1500
caaggtaacc gta                                                      1513
```

```
<210> SEQ ID NO 4
<211> LENGTH: 20
<212> TYPE: DNA
<213> ORGANISM: Artificial Sequence
<220> FEATURE:
<223> OTHER INFORMATION: Forward primer

<400> SEQUENCE: 4
agagtttgat catggctcag                                                20

<210> SEQ ID NO 5
<211> LENGTH: 22
<212> TYPE: DNA
<213> ORGANISM: Artificial Sequence
<220> FEATURE:
<223> OTHER INFORMATION: Reverse primer.

<400> SEQUENCE: 5
tacggttacc ttgttacgac tt                                             22

<210> SEQ ID NO 6
<211> LENGTH: 1617
<212> TYPE: DNA
<213> ORGANISM: Bacillus cereus CRCO-4
```

<400> SEQUENCE: 6

```
gcctgttagg gcgattgatt tagcggccgc gaattcgccc ttagagtttg atcatggctc      60
aggatgaacg ctggcggcgt gcctaataca tgcaagtcga gcgaatggat taagagcttg     120
ctcttatgaa gttagcggcg gacgggtgag taacacgtgg gtaacctgcc cataagactg     180
ggataactcc gggaaaccgg ggctaatacc ggataatatt ttgaactgca tggttcgaaa     240
ttgaaaggcg gcttcggctg tcacttatgg atggacccgc gtcgcattag ctagttggtg     300
aggtaacggc tcaccaaggc aacgatgcgt agccgacctg agagggtgat cggccacact     360
gggaccgaga cacggcccag actcctacgg gaggcagcag tagggaatct tccgcaatgg     420
acgaaagtct gacggagcaa cgccgcgtga gtgatgaagg ctttcgggtc gtaaaactct     480
gttgttaggg aagaacaagt gctagttgaa taagctggca ccttgacggt acctaaccag     540
aaagccacgg ctaactacgt gccagcagcc gcggtaatac gtaggtggca agcgttatcc     600
ggaattattg ggcgtaaagc gcgcgcaggt ggtttcttaa gtctgatgtg aaagcccacg     660
gctcaacccg tggagggtca ttggaaactg ggagacttga gtgcagaaga ggaaagtgga     720
attccatgtg tagcggtgaa atgcgtagag atatggagga acaccagtgg cgaaggcgac     780
tttctggtct gtaactgaca ctgaggcgcg aaagcgtggg gagcaaacag gattagatac     840
cctggtagtc cacgccgtaa acgatgagtg ctaagtgtta gagggtttcc gccctttagt     900
gctgaagtta acgcattaag cactccgcct ggggagtacg gccgcaaggc tgaaactcaa     960
aggaattgac gggggcccgc acaagcggtg gagcatgtgg tttaattcga agcaacgcga    1020
agaaccttac caggtcttga catcctctga aaacctagaa gatagggctt ctccttcggg    1080
agcagagtga caggtggtgc atggttgtcg tcagctcgtg tcgtgagatg ttgggttaag    1140
tcccgcaacg agcgcaaccc ttgatcttag ttgccatcat taagttgggc actctaaggt    1200
gactgccggt gacaaaccgg aggaaggtgg ggatgacgtc aaatcatcat gccccttatg    1260
acctgggcta cacacgtgct acaatggacg gtacaaagag ctgcaagacc gcgaggtgga    1320
gctaatctca taaaaccgtt ctcagttcgg attgtaggct gcaactcgcc tacatgaagc    1380
tggaatcgct agtaatcgcg gatcagcatg ccgcggtgaa tacgttcccg ggccttgtac    1440
acaccgcccg tcacaccacg agagtttgta cacccgaag tcggtggggt aacctttttg    1500
gagccagccg cctaaggtgg gacagatgat tgggtgaag tcgtaacaag gtaaccgtaa    1560
agggcgaatt cgtttaaacc tgcaggacta gtcccttag tgagggtaat ctggagc      1617
```

<210> SEQ ID NO 7
<211> LENGTH: 1616
<212> TYPE: DNA
<213> ORGANISM: Bacillus cereus CRCO-5

<400> SEQUENCE: 7

```
gtctagttag ggcgattgat ttagcggccg cgaattcgcc ctttacggtt accttgtacg      60
acttcacccc aatcatctgt cccaccttag gcggctggct ccaaaaaggt taccccaccg     120
acttcgggtg ttacaaactc tcgtggtgtg acgggcggtg tgtacaaggc ccgggaacgt     180
attcaccgcg gcatgctggt ccgcgattac tagcgattcc agcttcatgt aggcgagttg     240
cagcctacaa tccgaactga gaacggtttt atgagattag ctccacctcg cggtcttgca     300
gctctttgta ccgtccattg tagcacgtgt gtagcccagg tcataagggg catgatgatt     360
tgacgtcatc cccaccttcc tccggtttgt caccggcagt cacttagag tgcccaactt     420
aatgatggca actaagatca agggttgcgc tcgttgcggg acttaaccca acatctcacg     480
```

-continued

```
acacgagctg acgacaacca tgcaccacct gtcactctgc tcccgaagga gaagccctat    540
ctctagggtt ttcagaggat gtcaagacct ggtaaggttc ttcgcgttgc ttcgaattaa    600
accacatgct ccaccgcttg tgcgggcccc cgtcaattcc tttgagtttc agccttgcgg    660
cccgtactcc ccaggcggag tgcttaatgc gttaacttca gcactaaagg gcggaaaccc    720
tctaacactt agcactcatc gtttacggcg tggactacca gggtatctaa tcctgtttgc    780
tccccacgct ttcgcgcctc agtgtcagtt acagaccaga aagtcgcctt cgccactggt    840
gttcctccat atctctacgc atttcaccgc tacacatggg attccacttt cctcttctgc    900
actcaagtct cccagtttcc aatgaccctc cacggttgag ccgtgggctt tcacatcaga    960
cttaagaaac cacctgcgcg cgctttacgc ccaataattc cggataacgc ttgccaccta   1020
cgtattaccg cggctgctgg cacgtagtta gccgtggctt tctggttagg taccgtcaag   1080
gtgccagctt attcaactag cacttgttct tccctaacaa cagagtttta cgacccgaaa   1140
gccttcatca ctcacgcggc gttgctccgt cagactttcg tccattgcgg aagattccct   1200
actgctgcct cccgtaggag tctgggccgt gtctcagtcc cagtgtggcc gatcaccctc   1260
tcaggtcggc tacgcatcgt tgccttggtg agccgttacc tcaccaacta gctaatgcga   1320
cgcgggtcca tccataagtg acagccgaag ccgcctttca atttcgaacc atgcggttca   1380
aaatattatc cggtattagc cccggtttcc cggagttatc ccagtcttat gggcaggtta   1440
cccacgtgtt actcacccgt ccgccgctaa cttcataaga gcaagctctt aatccattcg   1500
ctcgacttgc atgtattagg cacgccgcca gcgttcatcc tgagccatga tcaaactcta   1560
agggcgaatt cgtttaaacc tgcaggacta gtccctttag tgaggataat ctggcg       1616
```

US 11,363,820 B2

METHOD FOR SELECTING PLANT SYMBIOTIC MICROBES, AND MICROBIAL MIXTURE

TECHNICAL FIELD

The present invention relates to a screening method for selecting plant symbiotic microorganisms enabling plant growth under abiotic stress (environmental stress) and/or biotic stress (disease stress), a microbial mixture of microorganisms which are selected out from nature by the screening method and enables plant growth under salinity stress in symbiosis with the plant, and a microbial mixture of microorganisms which are selected out from nature by the screening method and enables plant growth under hyperosmotic stress in symbiosis with the plant.

Priorities are claimed on U.S. Patent Application No. 62/431,443, filed Dec. 8, 2016, U.S. Patent Application No. 62/434,427, filed Dec. 15, 2016, U.S. Patent Application No. 62/449,118, filed Jan. 23, 2017, U.S. Patent Application No. 62/449,122, filed Jan. 23, 2017, and U.S. Patent Application No. 62/488,069, filed Apr. 21, 2017, the contents of which are incorporated herein by reference.

BACKGROUND ART

Some microorganisms live in symbiosis with plants to promote growth of the plants. For example, *Rhizobium* symbiotically living within the roots of legumes converts nitrogen in the atmosphere into nitrogen compounds that can be utilized by plants. Such nitrogen fixation by root nodule bacteria enables the legumes to grow even in soil with scarce nutrients. In recent years, it has been found that there are symbiotic microorganisms having abilities to enhance immune system of plants, promote growth, supplement the deficiency of nutrients, and increase tolerance against various abiotic stresses. Therefore, it has been attempted to utilize such symbiotic microorganisms to enable plant growth even in severe environments such as soil deficient in essential nutrients or soil with a high salt concentration.

Myriad microorganisms exist in the natural environments such as soil, which are expected to include many beneficial microorganisms that can live in symbiosis with plants. However, many microorganisms are "difficult-to-culture" microorganisms which are difficult to culture in generally used media and the like; therefore, only a very small portion of microorganisms belonging to the natural world can be isolated by generally used plate culture methods, and the benefits of the microorganisms cannot be investigated. As a method for separating such difficult-to-culture microorganisms from the natural world, for example, Patent Document 1 discloses a method in which microorganisms extracted from nature are caused to adhere to the roots of sterile duckweed (*Spirodela polyrrhiza*), and cultured in a liquid medium together with the sterile duckweed. The use of duckweed family plants as a support for culturing microorganisms enables acquiring microorganisms directly from a sample taken from nature, which could not have been separated and collected by a conventional method of separating microorganisms a plate culture method.

PRIOR ART REFERENCES

Patent Document

Patent Document 1: Japanese Unexamined Patent Application Publication No. 2009-195124

SUMMARY OF THE INVENTION

Problems to be Solved by the Invention

Conventionally, finding microorganisms beneficial for plant growth from nature has been carried out by a method in which microorganisms are first isolated from natural sources and, then, examined as to whether or not the isolated microorganisms are beneficial. For example, for finding microorganisms that enable plant growth under certain abiotic stress, microorganisms isolated from nature are inoculated onto plants and the plants are allowed to grow under the stress for a certain period of time. By collecting the microorganisms from the plants that have grown, beneficial symbiotic microorganisms of interest can be obtained.

However, some microorganisms exhibit beneficial effect only in the form of a specific microbial mixture, and it is laborious and very difficult to carry out experiments to investigate the benefits of numerous combinations of microorganisms. There is also a case where not all of microorganisms necessary for achieving the benefits are isolated.

In view of the above situation, the purpose of the present invention is to provide a screening method for selecting plant symbiotic microorganisms enabling plant growth under abiotic stress and/or biotic stress, a microbial mixture of microorganisms which are selected out from nature by the screening method and enables plant growth under salinity stress in symbiosis with the plant, and a microbial mixture of microorganisms which are selected out from nature by the screening method and enables plant growth under hyperosmotic stress in symbiosis with the plant.

Means to Solve the Problems

The screening method, the method for growing a plant and the microbial mixture according to the present invention are as enumerated below in [1] to [22].

[1] A screening method for selecting plant symbiotic microorganisms, comprising a first screening step of allowing at least one plant to grow for a predetermined period of time while being partially soaked in a solution containing a microbial mixture under application of at least one type of stress selected from the group consisting of abiotic stress and biotic stress, and collecting microorganisms adhering to grown plant to thereby select out the microorganisms as a group of plant symbiotic microorganisms enabling plant growth under the stress.

[2] The screening method according to [1], wherein the first screening step is followed by repeating at least once a cycle comprising a step (1) of allowing at least one plant to grow for a predetermined period of time while being partially soaked in a solution containing the selected microorganisms under application of the stress, and collecting microorganisms adhering to grown plant to thereby select out the microorganisms as plant symbiotic microorganisms enabling plant growth under the stress.

[3] The screening method according to [2], wherein intensity of the stress applied in the step (1) is increased in each cycle to a higher level than the stress applied in a previous cycle.

[4] The method according to [2] or [3], wherein, when the cycle is repeated twice or more, stress of a different type from the stress applied in the step (1) of a previous cycle is additionally applied in the step (1) of each cycle.

[5] The screening method according to [1], wherein the first screening step is followed by a first culture step of culturing the selected microorganisms in two or more culture media for a predetermined period of time, and mixing the microorganisms cultured in the respective culture media to thereby prepare a culture of a group of plant symbiotic microorganisms enabling plant growth under the stress.

[6] The method according to [5], wherein the first screening step is followed by repeating at least once a cycle comprising:
a step (1') of allowing at least one plant to grow for a predetermined period of time while being partially soaked in a solution containing the selected group of plant symbiotic microorganisms under application of the stress, and collecting microorganisms adhering to grown plant to thereby select out the microorganisms as a group of plant symbiotic microorganisms enabling plant growth under the stress; and
a step (2') of culturing the microorganisms selected in the step (1') in two or more culture media for a predetermined period of time, and mixing the microorganisms cultured in the respective culture media to thereby prepare a culture of a group of plant symbiotic microorganisms enabling plant growth under the stress.

[7] The method according to [6], wherein intensity of the stress applied in the step (1') is increased in each cycle to a higher level than the stress applied in a previous cycle.

[8] The method according to [6] or [7], wherein, when the cycle is repeated twice or more, stress of a different type from the stress applied in the step (1') of a previous cycle is additionally applied in the step (1') of each cycle.

[9] The method according to any one of [1] to [8], wherein intensity of the stress is such that a survival rate of the plant grown under aseptic condition is less than 50%.

[10] The method according to [2] or [6], wherein a root of the plant is soaked in a solution containing the microorganisms in the first screening step, the step (1) or the step (1').

[11] The method according to any one of [1] to [10], wherein the abiotic stress is salinity stress, hyperosmotic stress, nutritional stress, low temperature stress, or high temperature stress, and the biotic stress is stress caused by pathogenic bacteria or stress caused by pests.

[12] The method according to any one of [1] to [10], wherein the abiotic stress is at least two stresses selected from the group consisting of salinity stress, hyperosmotic stress, nutritional stress, low temperature stress, and high temperature stress.

[13] The method according to any one of [1] to [12], wherein the microorganisms in the solution in which at least a part of the plant is soaked in the first selection step are microorganisms extracted from one or more samples taken from nature.

[14] The method according to [13], wherein the sample is soil.

[15] A method for growing a plant, which comprises a growth step of allowing at least one plant to grow under the stress with the plant symbiotic bacteria selected by the method of any one of claims [1] to [14] being adhering to a root of the plant.

[16] The method according to [15], wherein the growth step is
a step of hydroponically growing the at least one plant under aseptic condition, attaching the microorganisms to a root of the plant, transferring the plant to soil, and allowing the plant to grow under the stress.

[17] A group of plant symbiotic microorganisms selected by the method of any one of [1] to [16].

[18] Microorganisms of one or more species, which are isolated from the group of plant symbiotic microorganisms selected by the method of any one of [1] to [16].

[19] A microbial mixture which enables a plant to grow under salinity stress in symbiosis with the plant, and comprises: *Bacillus pumilus* CRCO-1 strain having 16S rDNA with a nucleotide sequence represented by SEQ ID NO: 1,
*Bacillus pumilus* CRCO-2 strain having 16S rDNA with a nucleotide sequence represented by SEQ ID NO: 2, and
*Bacillus pumilus* CRCO-3 strain having 16S rDNA with a nucleotide sequence represented by SEQ ID NO: 3.

[20] The microbial mixture according to [19], wherein an abundance ratio of the *Bacillus pumilus* CRCO-1 strain is 70 to 90%, an abundance ratio of the *Bacillus pumilus* CRCO-2 strain is 5 to 20%, and an abundance ratio of the *Bacillus pumilus* CRCO-3 is 1 to 15%.

[21] A microbial mixture which enables a plant to grow under hyperosmotic stress in symbiosis with the plant, and comprises *Bacillus cereus* CRCO-4 strain having 16S rDNA with a nucleotide sequence represented by SEQ ID NO: 6, and *Bacillus cereus* CRCO-5 strain having 16S rDNA with a nucleotide sequence represented by SEQ ID NO: 7.

[22] The microbial mixture according to [21], wherein an abundance ratio of *Bacillus cereus* CRCO-4 strain is 80 to 95%, and an abundance ratio of *Bacillus cereus* CRCO-5 strain is 5 to 20%.

Effect of the Invention

The screening method of the present invention enables selection of an assembled group of plant symbiotic microorganisms which live in symbiosis with a plant and enables the plant to grow under abiotic stress and/or biotic stress.

Further, the microbial mixture of the present invention can improve the salt tolerance or hyperosmotic stress of a plant living in symbiosis with the microorganisms included in the microbial mixture. Therefore, the inoculation of a plant with the microbial mixture to allow for the symbiosis between the plant and the microorganisms can improve the viability of the plant grown under high salt concentration environment or hyperosmotic environment.

BRIEF DESCRIPTION OF THE DRAWINGS

FIG. 1 is a diagram schematically showing a pot 1 (shown at the left in the diagram) with seed 3 sowed in Reference Example 1 and a pot 1 (shown at the right in the diagram) with a plant 4 grown in Reference Example 1.

DESCRIPTION OF THE EMBODIMENTS

<Screening Method for Selecting Plant Symbiotic Microorganisms>

The screening method of present invention for selecting plant symbiotic microorganisms comprises a first screening step of allowing at least one plant to grow for a predetermined period of time while being partially soaked in a solution containing a microbial mixture under application of at least one type of stress selected from the group consisting of abiotic stress and biotic stress, and collecting microorganisms adhering to grown plant to thereby select out the microorganisms as plant symbiotic microorganisms enabling plant growth under the stress. Unlike a method of inoculating a plant with a plurality of microorganisms that has been isolated and mixed in advance to find a combination of microorganisms enabling the growth of the plant under stress, the screening method according to the present invention involves collecting a group of symbiotic microorganisms enabling plant growth under stress directly from a mixture of plural species of microorganisms; therefore, a group of beneficial symbiotic microorganisms can be selected relatively easily.

The microorganisms in the microbial mixture to be inoculated to the at least one plant in the first screening step is not particularly limited and may be those extracted from a sample taken from nature or may be those extracted from a sample taken from an artificial environment. In the present invention, the aforementioned microorganisms are preferably those extracted from a sample taken from nature. Examples of the sample taken from nature include soils of forests, wetlands, plains, cultivated lands and paddy fields; water and sediments of oceans, rivers, lakes and hot springs; and animals and plants. Examples of the sample taken from an artificial environment include samples taken from food factories, sewage treatment facilities, waste treatment facilities, hospitals, and the like. The extraction of microorganisms from these samples can be carried out by a conventional method.

In the present invention, the microbial mixture to be inoculated to the at least one plant may be a mixture of microorganisms extracted from one type of sample, or a mixture of microorganisms extracted from two or more types of samples. In the present invention, the at least one plant is inoculated with a suspension of the microorganisms extracted from a sample in a solution, and hence the microorganisms extracted from two or more types of samples can be brought into contact with the at least one plant by a single operation. For example, when five types of soils are used as samples, the microorganisms may be brought into contact with the at least one plant in any of the following manners: the microorganisms are extracted together with the soils to prepare respective suspensions, which are then brought into contact with the plant(s) separately; the microorganisms extracted together with the soils are suspended in a single solution, which is then brought into contact with the plant(s); or the soils are mixed together in advance to prepare a soil mixture, from which microorganisms are extracted to prepare a suspension, and the suspension is brought into contact with the plant(s). Bringing a mixture of microorganisms taken from a plural types of samples into contact with the at least one plant can reduce the labor required for selection of a group of plant symbiotic microorganisms, and is expected to make it easier to obtain a group of microorganisms having higher symbiotic effect.

The microorganisms to be inoculated to the at least one plant in the first screening step may be mutants of already isolated microorganisms. Examples of the mutation treatment for obtaining mutants include treatments with energy rays such as ultraviolet rays, X rays and gamma rays, and treatments with mutagens such as ethyl methanesulfonate (EMS), N-methyl-N-nitrosoguanidine (NTG), and nitrous acid. The screening method of the present invention enables easy selection of beneficial plant symbiotic microorganisms from the mutated microorganisms.

In the screening method of the present invention, a microbial mixture is contained in a solution in which the at least one plant are to be soaked (hereinafter, also referred to as "soaking solution"). The inoculation of the microbial mixture to the at least one plant in an aqueous medium allowing highly free movement of microorganisms rather than in a solid medium such as a plate medium facilitates formation of various combinations of microorganisms, which is likely to result in symbiosis of a group of beneficial microorganisms in or on the surface of the plants that enable plant growth under stress. In the present specification, the phrase "group of microorganisms" means a group of two or more species of microorganisms. The group of plant symbiotic microorganisms selected in the present invention may be a group of two or more different species of microorganisms or a group of microorganisms of two or more different strains belonging to the same species.

In the screening method of the present invention, at least a part of the at least one plant is soaked in a soaking solution containing the microbial mixture in order to inoculate the at least one plant with the microorganisms. The part of the plant to be soaked in the soaking solution may be any part as long as the part can grow if the soaked plants are free from abiotic stress and biotic stress, and may be, for example, any of root, stem, leaf, and rhizome.

In the present invention, it is preferable that only the roots of the at least one plant are soaked in the soaking solution containing the microbial mixture since the influence on the plant growth is relatively small. In this case, the soaking solution is preferably a liquid fertilizer containing nutrients to be taken from the roots. For example, at least one plant can be grown with only the roots thereof soaked in the soaking solution containing the microbial mixture by using a hydroponic container designed to have a base portion (upper end) of plant roots supported with a solid support such as a rock wool, an agar medium or a soil, and to have a lower part of the roots soaked in a liquid fertilizer, and by using a liquid fertilizer containing the microbial mixture. The composition of the liquid fertilizer to be used can be appropriately adjusted depending on the species of the plant(s) to be grown. For example, MS (Murashige-Skoog) medium, B5 (Gamborg's B 5) medium, White medium, or modified versions thereof can be used.

The species of the at least one plant used in the method of the present invention is not particularly limited, and any kind of plant can be used. In particular, it is highly likely that beneficial symbiotic microorganisms vary depending on the type of the plant; therefore, it is preferable to use a plant which is desired to be enabled to grow under the stress of interest. For example, if there is a crop plant that is desired to be grown in an area where plants suffer from severe salt damage, the screening method of the present invention may be implemented using that plant.

The at least one plant used in the screening method of the present invention is preferably one grown aseptically. For example, the use of a plant grown from a sterilized seed under aseptic condition can prevent unintended introduction of microorganisms from the plant. The sterilization treatment of the seed can be carried out by a conventional method such as a method of soaking the seed in a sodium hypochlorite solution, a method of using a chlorine gas or the like.

In the screening method of the present invention, one plant body may be soaked in one soaking solution containing microorganisms (i.e., a soaking solution containing microorganisms which is accommodated in one container); however, it is preferable to soak a plurality of plants in the soaking solution. Simultaneously inoculating a plurality of plants while allowing highly free movement of microorganisms increases opportunities for symbiosis of the microorganisms with the plants and facilitate efficient selection of beneficial microorganisms. In the present invention, the number of plants to be soaked in one soaking solution is preferably 8 or more, more preferably 24 or more, further preferably 48 or more, still more preferably 96 or more. When the at least one plant to be used is an aquatic plant or a plant capable of being grown hydroponically, roots of many plants can be soaked in a sufficient amount of soaking solution, which allows more efficient selection of symbiotic microorganisms.

In the present invention and the specification of the present application, the term "abiotic stress" embraces various stresses inflicted on the plants from the outside world. Examples of the abiotic stress include salinity stress (stress due to too high a salt concentration), drought stress (hyperosmotic stress), nutritional stress (stress due to deficiency or excess of necessary nutrients), low temperature stress (including freezing stress), and high temperature stress. Examples of the nutritional stress include stresses due to deficiency of nutrients essential for the plant growth, such as iron (Fe), manganese (Mn), boron (B), zinc (Zn), nickel (Ni), molybdenum (Mo), nitrogen (N), phosphorus (P), potassium (K), calcium (Ca), magnesium (Mg), and sulfur (S). Examples of other abiotic stresses include stresses due to the presence of toxic substances, such as aluminum stress which is a problem mainly caused by acidic soils. In the present invention and the specification of the present application, the term "biotic stress" embraces, for example, biological stresses caused by pathogenic bacteria, pests and the like.

For example, the salinity stress can be applied to the at least one plant to be grown by increasing the salt concentration of the soaking solution containing the microbial mixture. Likewise, the aluminum stress can be applied to the at least one plant to be grown by increasing the aluminum ion concentration of the soaking solution. Also, since the drought stress is mainly induced by a hyperosmotic pressure caused by drying, the drought stress can be applied by increasing the concentration of polyethylene glycol (PEG), mannitol, sucrose, etc. in the soaking solution so as to grow the at least one plant under hyperosmotic condition. On the other hand, the nutrient deficiency stress can be applied to the at least one plant to be grown by reducing the amount of essential nutrients in the soaking solution or using a soaking solution containing no nutrients. Further, the low temperature stress and high temperature stress can be applied to the at least one plant to be grown by controlling the ambient temperature at which the at least one plant are grown. Furthermore, the intensity of the biotic stress can be increased by increasing the amount of pathogenic bacteria and pests which are infectious to the plant.

In the screening method of the present invention, only one type of stress may be applied to the at least one plant to be grown, or two or more types of stress may be applied in combination. For example, the use of a soaking solution with increased concentrations of both of PEG etc. and salt enables the simultaneous application of salinity stress and drought stress to the at least one plant, whereby symbiotic microorganisms capable of imparting both the salt tolerance and the drought stress tolerance to the plant(s) can be selected. The combination of stresses is not particularly limited, and two or more abiotic stresses may be combined, or an abiotic stress and a biotic stress may be combined.

For efficiently selecting plant symbiotic microorganisms enabling plant growth under stress, the intensity of abiotic stress and/or biotic stress is preferably such that the stress exerts some influence on the phenotype, for example, such that the plant(s) cannot grow normally under aseptic condition and withers. The intensity is more preferably such that the plant growth itself is difficult under aseptic condition. More specifically, it is preferable that the intensity of the stress is such that a survival rate of the plant grown under aseptic condition is 0 to less than 50%, more preferably 0 to 30%. The intensity of stress within such a range enables more efficient selection of symbiotic microorganisms capable of imparting desired stress tolerance by symbiosis.

By allowing at least one plant to grow for a predetermined period of time while being soaked in a solution containing a microbial mixture under application of abiotic stress and/or biotic stress, microorganisms in a suitable combination are caused to symbiose with the plant(s). The period for plant growth is not particularly limited as long as it is sufficient for the influence of the stress on the plant(s) to be manifested, and can be appropriately set in consideration of the type of the plant(s), the type of stress, and the like. For example, when *Arabidopsis thaliana* is to be grown, the growth period under stress may range from 3 days to 1 month, preferably 7 to 21 days.

When grown under stress, plants in a aseptic state cannot grow normally; however, when a suitable group of symbiotic microorganisms is formed in the plants, the microorganisms act to facilitate the plant growth. In other words, when plants are grown under stress for a certain period of time while being soaked in a soaking solution containing a microbial mixture, the presence of plants that have grown normally or are obviously less affected by the stress than the other plants means that such plants are living in symbiosis with plant symbiotic microorganisms enabling plant growth under the stress. Therefore, microorganisms adhering to the plants grown for a certain period of time are collected, and are selected as plant symbiotic microorganisms enabling plant growth under the stress. The collection of microorganisms from the plants can be carried out by a conventional method. Further, the microorganisms may be separately collected from the grown plants, or may be collected together from all of the grown plants.

The plant symbiotic microorganisms selected in the first screening step are preferably those which can be cultured in a microbial culture medium generally used for culturing microorganisms since such microorganisms are excellent in handleability. Examples of the microbial culture medium include LB (Luria-Bertani) medium, TBS (Tryptic Soy Broth) medium, malt extract medium, oatmeal medium, YM (Yeast Malt peptone) medium, YPD (Yeast Peptone D-Glucose), NB (nutrient broth) medium, R2A medium, PGY medium, GYMP medium (glucose 1%, yeast extract 0.5%, malt extract 0.3%, peptone 0.5%, pH 6.0), MRS (de Man-Rogosa-Sharpe) medium, PSA (Potato Sucrose Agar) medium, and SWS (Seawater Starch Agar) medium.

Further, repeating the screening step to cause the symbiosis of the microorganisms with the plant(s) under stress can further optimize the type and abundance ratio of the microorganisms in the plant symbiotic microorganisms to be selected, thereby enabling the selection of plant symbiotic bacteria having higher symbiotic effect to facilitate the plant growth under stress. Specifically, the first screening step is followed by repeating at least once a cycle comprising a step (1) of allowing at least one plant to grow for a predetermined period of time while being partially soaked in a solution containing the selected microorganisms under application of the stress, and collecting microorganisms adhering to grown plant to thereby select out the microorganisms as plant symbiotic microorganisms enabling plant growth under the stress.

When the cycle is performed only once, the microorganisms selected in step (1) are a group of plant symbiotic microorganisms selected in the first screening step. When the cycle is repeated twice (two rounds), the microorganisms selected in step (1) is the plant symbiotic microorganisms selected in the step (1) of the previous round. For example, when the cycle is repeated three times, a group of microorganisms selected in step (1) of the first round is a group of plant symbiotic microorganisms selected in the screening step, and a group of microorganisms selected in step (1) of the second round is a group of plant symbiotic microorganisms selected in step (1) of the first round, and a group of microorganisms selected in step (1) of the third round is a group of plant symbiotic microorganisms selected in step (1) of the second round.

The microorganism selected in the first screening step is usually a mixture composed of microorganisms of different species. Many of the microorganisms are not identified or are difficult-to-culture microorganisms, and the type of microbial culture medium usable therefor is unknown. Therefore, when the microorganisms are cultured in a single type of microbial culture medium, microorganisms to which the nutrient composition of the medium is not suitable are caused to be eliminated. As a result, in many cases, the resulting culture is devoid of ability to enable plant growth under the stress of interest. In view of this, in the present invention, it is preferable to perform, after the first screening step, a first culture step of culturing the selected microorganisms in two or more culture media for a predetermined period of time, and mixing the microorganisms cultured in the respective culture media to thereby prepare a culture of a group of plant symbiotic microorganisms enabling plant growth under the stress. That is, in the screening method of the present invention, it is preferable that the first screening step is followed by a first culture step of culturing the selected microorganisms in two or more culture media for a predetermined period of time, and mixing the microorganisms cultured in the respective culture media to thereby prepare a culture of a group of plant symbiotic microorganisms enabling plant growth under the stress. By culturing in a plurality of microbial culture media having different nutritional compositions and mixing all the microorganisms grown in such microbial culture media to obtain a culture of the selected group of plant symbiotic microorganisms, it becomes possible to remarkably reduce the risk of eliminating one of more species of the microorganisms constituting the selected group of microorganisms.

The microbial culture media to be used for culturing a group of plant symbiotic bacteria selected in the screening step may be appropriately select from among microbial culture media generally used for culturing microorganisms. The microbial culture media may be any of those exemplified above. In general, the use of a microbial culture medium generally used for culturing microorganisms results in more selective selection of microorganisms culturable in a microbial culture medium generally used for culturing microorganisms as microorganisms constituting the selected group of microorganisms. This thereby enables selection of a group of plant symbiotic microorganisms which are more excellent in handling from among a group of plant symbiotic microorganisms having an ability to enable plant growth under the stress of interest.

In addition, even when the growth of microorganisms has been confirmed after culturing, it is preferable to reiterate the screening step in order to check whether it was actually possible to culture, in the first culture step, all species of microorganisms necessary for enabling plant growth under stress among the microorganisms included in the microbial mixture selected in the first screening step. Specifically, at least one plant is inoculated with a microbial mixture obtained by mixing all microorganisms cultured for a certain period of time in a plurality of microbial culture media to see whether the inoculated plant(s) can be grown under the same conditions as in the first screening step. That is, at least one plant is grown for a certain period under abiotic stress while being partially soaked in a solution containing a microbial mixture obtained by mixing cultures derived from a plurality of microbial culture media. If the plant has been successfully grown, it can be said that all of the microorganisms constituting a desired group of plant symbiotic microorganisms can be cultured by the microbial culture media used in the culture step. Microorganisms adhering to the grown plant(s) are collected and selected out as a group of plant symbiotic microorganisms enabling plant growth under stress.

Further, repeating the screening step to cause the symbiosis of the microorganisms with the plant(s) under stress and the subsequent culture step can further optimize the type and abundance ratio of the microorganisms in a group of plant symbiotic microorganisms to be selected, thereby enabling the selection of a group of plant symbiotic microorganisms having higher symbiotic effect to facilitate the plant growth under stress. Specifically, the first culture step is followed by repeating at least once a cycle comprising a step (1') of allowing at least one plant to grow for a predetermined period of time while being partially soaked in a solution containing the selected group of plant symbiotic microorganisms under application of the stress, and collecting microorganisms adhering to grown plant to thereby select out the microorganisms as a group of plant symbiotic microorganisms enabling plant growth under the stress; and a step (2') of culturing the microorganisms selected in the step (1') in two or more culture media for a predetermined period of time, and mixing the microorganisms cultured in the respective culture media to thereby prepare a culture of a group of plant symbiotic microorganisms enabling plant growth under the stress.

When the cycle is performed only once, the "culture of a group of plant symbiotic microorganisms" selected in step (1') is a culture of a group of plant symbiotic microorganisms prepared in the first culture step. When the cycle is performed twice (two rounds), the "culture of a group of plant symbiotic microorganisms" in the step (1') is a culture of a group of plant symbiotic microorganisms prepared in the step (2') of the previous round. For example, when the cycle is repeated three times, the "culture of a group of plant symbiotic microorganisms" in the step (1') of the first round is a group of plant symbiotic microorganisms prepared in the first culture step, and the "culture of a group of plant symbiotic microorganisms" in the step (1') of the second round is a group of plant symbiotic microorganisms prepared in the step (2') of the first round, and the "culture of a group of plant symbiotic microorganisms" in the step (1') of the third round is a group of plant symbiotic microorganisms prepared in the step (2') of the second round.

With respect to the type and number of plants to be used, the part of the plants to be soaked in the soaking solution containing the microorganisms, the type of stress, the period and conditions for growing the plants, etc. in the step (1) or the step (1'), the same applies as in the first screening step. In the step (2'), when the microorganisms are cultured in a plural types of microbial culture media, the microorganisms cultured in different types of microbial culture media may be separately added to soaking solutions and allowed to symbiose with the plant(s), or the microorganisms cultured in different types of microbial culture media may be added to a single soaking solution and allowed to symbiose with the plant(s).

In the step (1) or the step (1'), the intensity of the stress applied while growing the plant(s) may be the same as in the first screening step, but is preferably higher than in the first screening step. Similarly, when the cycle is repeated twice (two rounds) or more, it is preferable that intensity of the stress applied in the step (1) or the step (1') is increased in each cycle to a higher level than the stress applied in a previous cycle. When it is intended to select a group of plant symbiotic microorganisms enabling plant growth under stress of a specific intensity, more efficient selection of such a group of plant symbiotic microorganisms can be achieved by setting the intensity of stress applied in the first screening step at a relatively low level, followed by repeating the aforementioned cycle to finally perform the cycle with application of stress of the desired specific intensity, rather than by performing the first screening step with application of stress of the desired specific intensity. For example, when it is intended to finally select out a group of plant symbiotic microorganisms enabling plant growth under salinity stress of a salt concentration of 2% by mass, efficient selection of such a group of plant symbiotic microorganisms can be achieved by performing the first screening step under application of a salinity stress of a salt concentration of 1% by mass, followed by performing the step (1) or the step (1') of the first round cycle under application of a salinity stress of a salt concentration of 1.5% by mass, and then performing the step (1) of the step (1') of the second round cycle under application of a stress of a salt concentration of 2.0% by mass.

The cycle may further include other process step as well as the aforementioned step (1) or the step (1') and the step (2'). For example, the cycle may include a step of rinsing the microorganisms selected in the previous round prior to performing the step (1) or the step (1'). The liquid used for rinsing the microorganisms is not particularly limited, and may be the culture solution used for culturing in the step (1) or the step (1'), or a buffer solution such as a sodium phosphate buffer solution or the like.

When repeating the cycle including the above step (1) or the step (1') and the step (2'), the type of stress applied to the at least one plant in each cycle may be changed or stress may be added. For example, salinity stress may be applied in the first cycle and drought stress may be applied in the subsequent second cycle. Also, salinity stress may be applied in the first cycle, and both salinity stress and drought stress may be applied in the subsequent second cycle. The application of multiple stresses simultaneously or in different cycles enables selection of a group of plant symbiotic microorganisms capable of imparting the multi-stress tolerance to the plant(s).

A group of plant symbiotic microorganisms capable of imparting multi-stress tolerance to the plant(s) can also be selected by repeating the screening method of the present invention while varying the type of stress. For example, a group of plant symbiotic microorganisms capable of imparting tolerance against both salinity stress and drying stress can be selected as follows. First, a group of plant symbiotic microorganisms is selected by the method of the present invention using a soaking solution having an increased salt concentration. By subjecting the resulting plants with the selected group of the plant symbiotic microorganisms adhering thereto to the screening method of the present invention using a soaking solution in which both the concentration of PEG etc. and the salt concentration are increased, it is possible to select a group of symbiotic microorganisms capable of imparting tolerance against both salinity stress and drought stress. The microbial mixture to be contacted with the plant(s) only under the initial salinity stress and the microbial mixture to be contacted subsequently with the plant(s) under both the salinity stress and the drought stress may be the same or may be those respectively extracted from different samples.

In the screening method of the present invention, the selection may be based on a specific phenotype of the grown plant, instead of a mere fact that the plant(s) has grown. For example, some plants, when grown under salinity stress, show a phenotype such as larger leaves, faster maturation, increased yields of fruits and the like. Therefore, when selecting a group of plant symbiotic microorganisms enabling plant growth under salinity stress by the screening method of the present invention, it is possible to select a group of plant symbiotic microorganisms enabling growth of a plant(s) exhibiting the specific phenotype under salinity stress by collecting microorganisms only from the plant(s) exhibiting the phenotype of interest in the first screening step, the step (1) or the step (1').

The stress tolerance of a plant can be remarkably improved by symbiosis with the group of plant symbiotic microorganisms selected by the screening method of the present invention. That is, the plant(s) can be grown under stress with the selected group of plant symbiotic microorganisms adhering to the roots thereof. In the present invention, the selected group of plant symbiotic microorganisms are preferably attached to the root since it is relatively easy to cause the microorganisms to contact and symbiose with the plant(s). With respect to the plant(s) to be grown under stress, the group of plant symbiotic microorganisms may be allowed to symbiose with not only plant(s) of the same kind as used in the screening step, but also plant(s) of a different kind from the plant(s) used in the screening step. Further, the cultivation of the plant(s) after initiating symbiosis with a group of plant symbiotic microorganisms may be carried out by hydroponics or in soil or the like. For example, after hydroponically growing the plant(s) in aseptic condition, the plant(s) with a selected group of plant symbiotic microorganisms adhering to the roots thereof may be transplanted into soil and allowed to grow under stress.

<Salt Tolerant Symbiotic Microorganisms>

The first microbial mixture according to the present invention enables plant growth under salinity stress in symbiosis with a plant(s) and includes *Bacillus pumilus* CRCO-1 strain having 16S rDNA with a base sequence represented by SEQ ID NO: 1, *Bacillus pumilus* CRCO-2 strain having 16S rDNA with a base sequence represented by SEQ ID NO: 2, and *Bacillus pumilus* CRCO-3 strain having 16S rDNA with a base sequence represented by SEQ ID NO: 3. The microbial mixture containing these three strains has been selected from those derived from soil by the screening method of the present invention as a group of plant symbiotic microorganisms enabling plant growth under salinity stress in symbiosis with the plant(s).

The results of the search of the base sequence of 16S rDNA by BLAST (Basic Local Alignment Search Tool) revealed that the *Bacillus pumilus* CRCO-1 strain and the *Bacillus pumilus* CRCO-2 strain had no 100% match, and both had a sequence homology of 99% or more relative to *Bacillus pumilus* (accession number: KF923448.1). It was thereby confirmed that each of *Bacillus pumilus* CRCO-1 strain and the *Bacillus pumilus* CRCO-2 strain was a novel strain of *Bacillus pumilus*. It was also found that the *Bacillus pumilus* CRCO-3 strain had a base sequence of 16S rDNA that was 100% identical to *Bacillus pumilus* (accession number: KF 923448.1) and, hence, was a known strain of *Bacillus pumilus*. *Bacillus pumilus* is a microorganism that is generally present in soil. Since *Bacillus pumilus* CRCO-1 strain and *Bacillus pumilus* CRCO-2 strain had a sequence homology of 99% or more in the base sequence of 16S rDNA, these strains were inferred to be closely related species of Uncultured *Bacillus* sp. (accession number: HM 152710.1) registered in NCBI (National Center for Biotechnology Information). This microorganism is a difficult-to-culture microorganism with only its genes known.

The abundance ratios (ratios of the numbers of bacteria) of *Bacillus pumilus* CRCO-1 strain, *Bacillus pumilus* CRCO-2 strain and *Bacillus pumilus* CRCO-3 strain in the first microbial mixture according to the present invention are not particularly limited. The abundance ratio of *Bacillus pumilus* CRCO-1 strain in the first microbial mixture according to the present invention is preferably 70 to 90%, more preferably 75 to 85%. The abundance ratio of *Bacillus pumilus* CRCO-2 strain in the first microbial mixture according to the present invention is preferably 5 to 20%, more preferably 5 to 15%. The abundance ratio of *Bacillus pumilus* CRCO-3 strain in the microbial mixture according to the present invention is preferably 1 to 15%, more preferably 1 to 10%.

The first microbial mixture according to the present invention may contain other microorganisms as long as such other microorganisms do not impair the effect of the microbial mixture that enhances the salt tolerance by symbiosis with the plant(s). The abundance ratio of the sum of *Bacillus pumilus* CRCO-1 strain, *Bacillus pumilus* CRCO-2 strain and *Bacillus pumilus* CRCO-3 strain to the total of the first microbial mixture according to the present invention is preferably 50% or more, more preferably 80% or more, still more preferably 90% or more. Particularly preferred as the first microorganism mixture according to the present invention is one consisting of *Bacillus pumilus* CRCO-1 strain, *Bacillus pumilus* CRCO-2 strain and *Bacillus pumilus* CRCO-3 strain.

<Hyperosmosis Tolerant Symbiotic Microorganisms>

The second microbial mixture according to the present invention enables plant growth under hyperosmotic stress in symbiosis with a plant(s) and includes *Bacillus cereus* CRCO-4 strain having 16S rDNA with a base sequence represented by SEQ ID NO: 6, and *Bacillus cereus* CRCO-5 strain having 16S rDNA with a base sequence represented by SEQ ID NO: 7. The microbial mixture containing these two strains has been selected from those derived from soil by the screening method of the present invention as a group of plant symbiotic microorganisms enabling plant growth under hyperosmotic stress caused by 20% PEG in symbiosis with the plant(s).

The results of the search of the base sequence of 16S rDNA by BLAST revealed that the *Bacillus cereus* CRCO-4 strain and the *Bacillus cereus* CRCO-5 strain had no 100% match, and both had a sequence homology of 99% or more relative to a known strain of *Bacillus cereus*. It is thereby inferred that each of *Bacillus cereus* CRCO-4 strain and the *Bacillus cereus* CRCO-5 strain is a novel strain of *Bacillus cereus*.

The abundance ratios (ratios of the numbers of bacteria) of *Bacillus cereus* CRCO-4 strain and *Bacillus cereus* CRCO-5 strain in the second microbial mixture according to the present invention is not particularly limited. The abundance ratio of *Bacillus cereus* CRCO-4 strain in the second microbial mixture according to the present invention is preferably 80 to 95%, more preferably 85 to 95%. The abundance ratio of *Bacillus cereus* CRCO-5 strain in the second microbial mixture according to the present invention is preferably 5 to 20%, more preferably 5 to 15%.

The second microbial mixture according to the present invention may contain other microorganisms as long as such other microorganisms do not impair the effect of the microbial mixture that enhances the hyperosmosis tolerance by symbiosis with the plant(s). The abundance ratio of the sum of the *Bacillus cereus* CRCO-4 strain and the *Bacillus cereus* CRCO-5 strain in the second microbial mixture according to the present invention is preferably 50% or more, more preferably 80% or more, and still more preferably 90% or more. Particularly preferred as the microbial mixture according to the present invention is one consisting of *Bacillus cereus* CRCO-4 strain and *Bacillus cereus* CRCO-5 strain.

EXAMPLES

Hereinbelow, the present invention will be described with reference to Examples which, however, should not be construed as limiting the present invention.

Reference Example 1

The salinity stress tolerance of *Arabidopsis thaliana* was examined.

<Preparation of Pots>

A sucrose-containing MS agar medium (medium prepared by adding 0.5% (w/v) sucrose and 0.9% (w/v) agar to a MS medium) was injected into a cylindrical pot with open top and bottom, and the agar medium was solidified to prepare a pot for growing a plant. A plurality of the thus prepared pots were placed in each of eight containers containing a sucrose-containing MS medium (liquid medium prepared by adding 0.5% (w/v) sucrose to a MS medium).

<Hydroponic Cultivation of Plant>

*Arabidopsis thaliana* seeds (Col-0) were purchased from LEHLE (Round Rock, Tex., USA). The seeds were stirred for 1 minute while being immersed in 1% hypochlorous acid solution to thereby sterilize the surfaces of the seeds, followed by removal of hypochlorous acid by centrifugation. After the hypochlorous acid treatment, the seeds were rinsed three times with sterilized water, sown on the top of the pot, and stored in a dark place at 4° C. for 24 hours.

Each of the pots was installed such that the bottom surface thereof was soaked in the sucrose-containing MS medium while the top surface thereof was not soaked. Then, the seeds sown in each pot was grown at 25° C. for 14 days in an incubator under long day conditions with 16 hours of light and 8 hours of darkness. The seeds germinated about 3 to 4 days after starting the growth in the incubator. FIG. 1 schematically shows the sowing in the pots (left) and the grown plants (right). After germination, the root (4a) of the plant grew through the solid medium and penetrated the bottom of the pot.

<Confirmation of Salinity Stress Tolerance of *Arabidopsis thaliana*>

14 days after initiating the hydroponics, with respect to six containers out of eight containers in which the pots were disposed, a sterilized 5 M sodium chloride aqueous solution was added to the sucrose-containing MS medium in each of the containers, such that the final concentrations of sodium chloride in the containers became 0.5, 1.0, 1.5, 2.0, 2.5 and 3.0 by mass, respectively. No sodium chloride aqueous solution was added to the remaining two of the eight containers (i.e., the final concentration of sodium chloride was 0% by mass). Thereafter, the pots were cultured for 14 days.

As a result, the plants appeared to have grown normally in the pots in which the sodium chloride concentration of the sucrose-containing MS medium soaking the roots of *Arabidopsis thaliana* was 0.5% by mass, as in the case of the plants grown in the pots in which the sodium chloride concentration was 0%. On the other hand, only a portion of the plants had grown in the pots in which the sodium chloride concentration of the sucrose-containing MS medium soaking the roots was 1.0% by mass or more. Specifically, 25.0% of the plants grew and survived at the sodium chloride concentration of 1.0% by mass, 16.7% of the plants grew and survived at the sodium chloride concentration of 1.5% by mass, no plants grew and survived at the sodium chloride concentration of 2.0% by mass, 8.3% of the plants grew and survived at the sodium chloride concentration of 2.5% by mass, and no plants grew and survived at the sodium chloride concentration of 3.0% by mass. These results show that *Arabidopsis thaliana* suffers from salinity stress when the salt concentration is 1.0% by mass or more.

Example 1

Using *Arabidopsis thaliana*, a group of plant symbiotic bacteria having a symbiotic effect to increase salt tolerance was selected from microorganisms extracted from the soil.
<Preparation of Microbial Suspension>
1 g of soil collected in Coyote Ridge (Fort Collins, Colo., USA) was suspended in a buffer solution, and the resulting was thoroughly stirred to obtain a microbial suspension.
<Hydroponic Cultivation of Plant>
As in Reference Example 1, a plurality of the above pots were prepared and all of them were placed in one container containing a sucrose-containing MS medium (liquid medium prepared by adding 0.5% (w/v) sucrose to a MS medium). Each pot was installed such that the bottom surface thereof was soaked in the sucrose-containing MS medium while the top surface thereof was not soaked. On the top of these pots, the seeds were sown and grown at 25° C. for 14 days in an incubator under long day conditions with 16 hours of light and 8 hours of darkness.
<Salinity Stress and Inoculation of Microorganisms (First Screening Step)>
14 days after initiating the hydroponic cultivation, a sterilized 5 M sodium chloride aqueous solution was added to the sucrose-containing MS medium in which the bottom of the pot was soaked, such that the final concentration of sodium chloride became 1% by mass, followed by addition of 100 µl of the microbial suspension. Thereafter, the pots were cultured for 14 days.
<Collection of Microorganisms from Grown Plant>
After cultivation under salinity stress for 14 days, the roots and the above-ground parts (leaves and stems) of the growing plants were cut, and the roots were collected and homogenized to obtain a microbial collection solution.
<Culturing of Microorganisms (First Culture Step)>
20 µL of the microbial collection solution was shake-cultured (200 rpm) overnight at 30° C. in 2 mL each of two kinds of media. The number of bacteria in the culture broth after culturing was $10^7$ CFU or more for each medium. The resulting cultures were mixed to obtain a microbial mixture solution.
<Salinity Stress and Inoculation of Microorganisms (Step (1) of 1st Round)>
First, plants which had been hydroponically grown by pots for 14 days were prepared in the same manner as in the above <Hydroponic Cultivation of Plant>. A sterilized 5 M sodium chloride aqueous solution was added to the sucrose-containing MS medium soaking the bottom of the pot, such that the final concentration of sodium chloride became 1.5% by mass, followed by addition of 100 µl of the microbial mixture solution prepared in the first culture step. Thereafter, the pots were cultured for 14 days.

After 14 days of culture under salinity stress, 6.3% of the plants grew and survived, 33.3% of the plants were dying, and 60.4% of the plants were dead (completely withered).

In the same manner as in the first screening step, the roots were recovered from the grown plant and homogenized to prepare a microbial collection solution.
<Culturing of Microorganisms (Step (2) of 1st Round)>
In the same manner as in the first cultivation step, the microbial collection solution prepared in step (1) of the first round was cultured in two kinds of media, and the resultant cultures were mixed to obtain a microbial mixture solution.
<Salinity Stress and Inoculation of Microorganisms (Step (1) of 2nd Round)>
The plants hydroponically grown in the pots for 14 days were grown under salinity stress for another 14 days in the same manner as in step (1) of the first round except that the final concentration of sodium chloride in the sucrose-containing MS medium soaking the bottom of the pot was set to 3.0% by mass instead of 1.5% by mass, and the microbial collection solution added to the sucrose-containing MS medium was changed to the microbial collection solution prepared in step (2) of the first round in place of the microbial collection solution prepared in the first screening step. Then, the roots were recovered from the grown plant and homogenized to prepare a microbial collection solution in the same manner as in step (1) of the first round.

After 14 days of cultivation under salinity stress, 1% of the plants grew and survived, 20.8% of the plants were dying, and 78.1% of the plants were dead.

These results revealed that the microbial mixtures living in symbiosis with the plants grown under salinity stress with the salt concentrations of 1.5 or 3.0% by mass had enabled growth of plants such as *Arabidopsis thaliana* under salinity stress. That is, by the screening method of the present invention, a group of plant symbiotic microorganisms enabling plant growth under salinity stress could be selected out from a microbial mixture in the soil.

Example 2

The microorganisms forming the group of plant symbiotic bacteria (microbial mixture) selected in Example 1 that enable plant growth under salinity stress were identified. Specifically, genomic DNA is recovered from the selected group of plant symbiotic bacteria (microbial mixture) that enables plant growth under salinity stress, and 16S rDNA was identified, thereby identifying microorganisms constituting the group of plant symbiotic bacteria.
<Recovery of Genomic DNA from Microbial Mixture>
In the same manner as in the above <Collection of Microorganisms from Grown Plant>, the roots were recovered from the plants grown under salinity stress with a salt concentration of 3.0% by mass and homogenized to prepare a microbial collection solution. Bacterial cells were recovered from the microbial collection solution, and a genomic DNA was obtained from a part of the recovered cells using a GenElute Bacterial Genomic DNA kit (Sigma-Aldrich, St. Louis, Mo., USA).
<Identification of 16S rDNA>
Using the recovered genomic DNA as a template, 16S rDNA was amplified by PCR using a forward primer (5'-AGAGTTTGATCATGGCTCAG-3', SEQ ID NO: 4) and a reverse primer (5'-TACGGTTACCTTGTTACGACTT-3', SEQ ID NO: 5). The temperature conditions of PCR were as follows: a heating step at 95° C. for 3 minutes; subsequent 30 cycles of a sequence of a denaturation step at 95° C. for 30 seconds, an annealing step at 50° C. for 30 seconds, and an elongation step at 72° C. for 1 minute and 30 seconds; and a final elongation reaction at 72° C. for 5 minutes. The obtained PCR product was confirmed by 1.2% agarose gel electrophoresis and extracted from the gel using a QIAquick gel extraction kit (Quiagen, Germantown, Md., USA). The extracted PCR product was inserted into a plasmid using TOPO-TA cloning kit (Life Technologies, Carlsbad, Calif., USA), and transformed into E. coli. Thirty (30) E. coli colonies cultured overnight on ampicillin-containing LB plate medium were randomly picked and transplanted into ampicillin-containing LB liquid medium, followed by culturing. A plasmid was purified from E. coli cultured using QIAprep spin miniprep kit (Quiagen). The purified plasmid was subjected to Thermalcycle reaction using BigDye terminator v3.1 Cycle sequence kit (Life Techonologies), and the base sequence of 16S rDNA inserted in the plasmid was determined with a DNA sequencer (ABI 3130xL).

As a result, three types of 16S rDNA (CRCO-1 stain, CRCO-2 strain, and CRCO-3 strain) were identified.

NCBI BLAST search was conducted for the base sequences of three types of 16S rDNAs, the sequences of which had been determined. As a result, CRCO-1 strain had a sequence homology of 99.93% with Uncultured Bacillus sp. (accession number: HM152710.1) and had a sequence homology of 99.87% with Bacillus pumilus (accession number: KF923448.1), CRCO-2 strain had a sequence homology of 99.87% with Uncultured Bacillus sp. (accession number: HM152710.1) and had a sequence homology of 99.80% with Bacillus pumilus (accession number: KF923448.1), and CRCO-3 strain had a sequence homology of 100% with Bacillus pumilus (accession number: KF923448.1). From these results, it was found that CRCO-1 stain and CRCO-2 strain are novel strains of Bacillus pumilus, and CRCO-3 stain is a known strain of Bacillus pumilus. That is, it was found that the group of plant symbiotic bacteria was formed of novel strains of Bacillus pumilus, i.e., CRCO-1 strain and CRCO-2 strain, and a known strain of Bacillus pumilus, i.e., CRCO-3 strain (accession number: KF923448.1).

Further, when the abundance ratio of these three types of microorganisms was examined from the ratio of 16S rDNA inserted in the identified 30 transformants, the abundance ratio of the Bacillus pumilus CRCO-1 strain was found to be 82.1%, the abundance ratio of the Bacillus pumilus CRCO-2 strain was found to be 10.7%, and the abundance ratio of the Bacillus pumilus CRCO-3 strain was found to be 7.1%.

<Identified Microbial Mixture's Symbiotic Effect Enhancing Salt Tolerance>

First, plants which had been hydroponically grown by pots for 14 days were prepared in the same manner as in the above <Hydroponic Cultivation of Plant>. A sterilized 5 M sodium chloride aqueous solution was added to the sucrose-containing MS medium soaking the bottom of the pot, such that the final concentration of sodium chloride became 3.0% by mass, followed by addition of a part of the bacterial cells recovered in the above <Recovery of Genomic DNA from Microbial Mixture>. Thereafter, the pots were cultured for 14 days.

After 14 days of culture under salinity stress, 3.1% of the plants were dead and 15.6% of the plants were dying, while the remainder of the plants grew and survived. The leaves of all of the dead plants turned white before withering.

Example 3

Using Arabidopsis thaliana, a group of plant symbiotic bacteria having a symbiotic effect to enhance hyperosmosis tolerance was selected from microorganisms extracted from the soil.

<Preparation of Microbial Suspension>

1 g of soil collected in Coyote Ridge (Fort Collins, Colo., USA) was suspended in a buffer solution, and the resulting was thoroughly stirred to obtain a microbial suspension.

<Hydroponic Cultivation of Plant>

As in Reference Example 1, a plurality of the above pots were prepared and all of them were placed in one container containing a sucrose-containing MS medium (liquid medium prepared by adding 0.5% (w/v) sucrose to a MS medium). Each pot was installed such that the bottom surface thereof was soaked in the sucrose-containing MS medium while the top surface thereof was not soaked. On the top of these pots, the seeds were sown and grown at 25° C. for 14 days in an incubator under long day conditions with 16 hours of light and 8 hours of darkness.

<High Concentration PEG Stress and Inoculation of Microorganisms (First Screening Step)>

14 days after initiating the hydroponic cultivation, a sterilized high-concentration aqueous PEG solution was added to the sucrose-containing MS medium soaking the bottom of the pot, such that the final concentration of PEG became 20% by mass, followed by addition of 100 μl of the microbial suspension. Thereafter, the pots were cultured for 14 days.

<Collection of Microorganisms from Grown Plant>

After cultivation under high concentration PEG stress for 14 days, the roots and the above-ground parts (leaves and stems) of the grown plants were cut, and the roots were collected and homogenized to obtain a microbial collection solution. All of the plants of Arabidopsis thaliana grown for 14 days under high concentration PEG stress in the absence of the microbial suspension were dead.

<Culturing of Microorganisms (First Culture Step)>

20 μL of the microbial collection solution was shake-cultured (200 rpm) overnight at 30° C. in 2 mL each of two kinds of media. The number of bacteria in the culture broth after culturing was $10^7$ CFU or more for each medium. The resulting cultures were mixed to obtain a microbial mixture solution.

<High Concentration PEG Stress and Inoculation of Microorganisms (Step (1) of 1st Round)>

First, plants which had been hydroponically grown by pots for 14 days were prepared in the same manner as in the above <Hydroponic Cultivation of Plant>. A sterilized high concentration PEG aqueous solution was added to the sucrose-containing MS medium soaking the bottom of the pot, such that the final concentration of PEG became 20% by mass, followed by addition of 100 μl of the microbial mixture solution prepared in the first culture step. Thereafter, the pots were cultured for 14 days.

<Recovery of Genomic DNA from Microbial Mixture>

In the same manner as in the above <Collection of Microorganisms from Grown Plant>, the roots were recovered from the plants grown under high concentration PEG stress and homogenized to prepare a microbial collection solution.

Bacterial cells were recovered from the microbial collection solution, and a genomic DNA was obtained from a part of the recovered cells using a GenElute Bacterial Genomic DNA kit (Sigma-Aldrich, St. Louis, Mo., USA). From the microbial collection solution, genomic DNA is recovered, and 16S rDNA was identified, thereby identifying microorganisms constituting the group of plant symbiotic bacteria (microbial mixture) that enables plant growth under high concentration PEG stress.

<Identification of 16S rDNA>

Using the recovered genomic DNA as a template, 16S rDNA was amplified by PCR in the same manner as in Example 2 to determine the base sequence of 16S rDNA of the resulting PCR product. As a result, two types of 16S rDNA (CRCO-4 strand and CRCO-5 strain) were identified. NCBI BLAST search was conducted for the base sequences of both types of 16S rDNAs. As a result, CRCO-4 strain had a sequence homology of 99.74% with *Bacillus cereus* partial 16S rRNA gene, strain M87 (accession number: LN890173), and CRCO-5 strain had a sequence homology of 99.61% with *Bacillus cereus* partial 16S rRNA gene, strain L68 (accession number: LN890064). From these results, it was found that CRCO-4 stain and CRCO-5 strain are strains of *Bacillus cereus*. That is, it was found that the group of plant symbiotic bacteria was formed of novel strains of *Bacillus cereus*, i.e., CRCO-4 strain and CRCO-5 strain.

Further, when the abundance ratio of these two types of microorganisms was examined from the ratio of 16S rDNA inserted in the identified 30 transformants, the abundance ratio of the *Bacillus cereus* CRCO-4 strain was found to be 90%, and the abundance ratio of the *Bacillus cereus* CRCO-5 strain was found to be 10%.

DESCRIPTION OF THE REFERENCE SIGNS

1 Pot
2 Sucrose-containing MS medium
3 Seed
4 Plant
4a Root

The invention claimed is:

1. A screening method for selecting plant symbiotic microorganisms, comprising implementing steps (i), (ii) and (iii) in this order:
   (i) a first screening step of allowing at least one plant to grow for a predetermined period of time while being partially soaked in a solution containing a microbial mixture under application of at least one type of stress selected from the group consisting of abiotic stress and biotic stress, and collecting microorganisms adhering to grown plant to thereby select out the microorganisms as a group of plant symbiotic microorganisms enabling plant growth under the stress,
   (ii) a first culture step of culturing the selected microorganisms, having been grown under the application of the at least one type of stress, in two or more different culture media appropriate for the growth of two or more selected microorganisms for a predetermined period of time, and
   (iii) mixing the microorganisms cultured in the respective culture media to thereby prepare a culture of a group of plant symbiotic microorganisms enabling plant growth under the stress.

2. The screening method according to claim 1, wherein the first screening step is followed by repeating at least once a cycle comprising a step (1) of allowing at least one plant to grow for a predetermined period of time while being partially soaked in a solution containing the selected microorganisms under application of the stress, and collecting microorganisms adhering to grown plant to thereby select out the microorganisms as a group of plant symbiotic microorganisms enabling plant growth under the stress.

3. The method according to claim 2, wherein intensity of the stress applied in the step (1) is increased in each cycle to a higher level than the stress applied in a previous cycle.

4. The method according to claim 2, wherein, when the cycle is repeated twice or more, stress of a different type from the stress applied in the step (1) of a previous cycle is additionally applied in the step (1) of each cycle.

5. The method according to claim 2, wherein a root of the plant is soaked in a solution containing the microorganisms in the first screening step, the step (1) or the step (1').

6. The method according to claim 1, wherein the first screening step is followed by repeating at least once a cycle comprising:
   a step (1') of allowing at least one plant to grow for a predetermined period of time while being partially soaked in a solution containing the selected group of plant symbiotic microorganisms under application of the stress, and collecting microorganisms adhering to grown plant to thereby select out the microorganisms as a group of plant symbiotic microorganisms enabling plant growth under the stress; and
   a step (2') of culturing the microorganisms selected in the step (1') in two or more culture media for a predetermined period of time, and mixing the microorganisms cultured in the respective culture media to thereby prepare a culture of a group of plant symbiotic microorganisms enabling plant growth under the stress.

7. The method according to claim 6, wherein intensity of the stress applied in the step (1') is increased in each cycle to a higher level than the stress applied in a previous cycle.

8. The method according to claim 6, wherein, when the cycle is repeated twice or more, stress of a different type from the stress applied in the step (1') of a previous cycle is additionally applied in the step (1') of each cycle.

9. The method according to claim 1, wherein intensity of the abiotic stress is such that a survival rate of the plant grown under aseptic condition is less than 50%.

10. The method according to claim 1, wherein the abiotic stress is salinity stress, hyperosmotic stress, nutritional stress, low temperature stress, or high temperature stress, and the biotic stress is stress caused by pathogenic bacteria or stress caused by pests.

11. The method according to claim 1, wherein the abiotic stress is at least two stresses selected from the group consisting of salinity stress, hyperosmotic stress, nutritional stress, low temperature stress, and high temperature stress.

12. The method according to claim 1, wherein the microorganisms in the solution in which at least a part of the plant is soaked in the first selection step are microorganisms extracted from one or more samples taken from nature.

13. The method according to claim 12, wherein the sample is soil.

14. A method for growing a plant, which comprises a growth step of allowing at least one plant to grow under the stress with the plant symbiotic bacteria selected by the method of claim 1 being adhering to a root of the plant.

15. The method according to claim 14, wherein the growth step is a step of hydroponically growing the at least one plant under aseptic condition, attaching the microorganisms to a root of the plant, transferring the plant to soil, and allowing the plant to grow under the stress.

* * * * *